(12) United States Patent
Wen

(10) Patent No.: US 10,335,250 B2
(45) Date of Patent: Jul. 2, 2019

(54) THREE-DIMENSIONAL PRINTED DENTAL APPLIANCES USING LATTICES

(71) Applicant: uLab Systems, Inc., Menlo Park, CA (US)

(72) Inventor: Huafeng Wen, Redwood Shores, CA (US)

(73) Assignee: uLab Systems, Inc., Redwood City, CA (US)

(*) Notice: Subject to any disclaimer, the term of this patent is extended or adjusted under 35 U.S.C. 154(b) by 26 days.

(21) Appl. No.: 15/230,193

(22) Filed: Aug. 5, 2016

(65) Prior Publication Data

US 2017/0100209 A1    Apr. 13, 2017

Related U.S. Application Data

(60) Provisional application No. 62/238,532, filed on Oct. 7, 2015.

(51) Int. Cl.
A61C 7/08 (2006.01)
A61C 7/00 (2006.01)
A61C 9/00 (2006.01)

(52) U.S. Cl.
CPC .............. A61C 7/002 (2013.01); A61C 7/08 (2013.01); A61C 9/004 (2013.01)

(58) Field of Classification Search
CPC .......... A61C 7/0002; A61C 7/08; A61C 7/002
See application file for complete search history.

(56) References Cited

U.S. PATENT DOCUMENTS

| 4,068,379 A | 1/1978 | Miller et al. |
| 4,889,485 A | 12/1989 | Iida |
| 4,983,334 A * | 1/1991 | Adell ................. A61C 7/08 264/138 |
| 5,055,039 A | 10/1991 | Abbatte et al. |
| 5,186,623 A | 2/1993 | Breads et al. |
| 5,691,905 A | 11/1997 | Dehoff et al. |
| 5,975,893 A | 11/1999 | Chishti et al. |
| 6,183,248 B1 | 2/2001 | Chishti et al. |
| 6,210,162 B1 | 4/2001 | Chishti et al. |
| 6,217,325 B1 | 4/2001 | Chishti et al. |
| 6,227,850 B1 | 5/2001 | Chishti et al. |
| 6,227,851 B1 | 5/2001 | Chishti et al. |
| 6,299,440 B1 | 10/2001 | Phan et al. |

(Continued)

FOREIGN PATENT DOCUMENTS

WO  WO 2006/050452  5/2006
WO  WO 2006/096558  9/2006

(Continued)

Primary Examiner — Ralph A Lewis
(74) Attorney, Agent, or Firm — Levine Bagade Han LLP

(57) ABSTRACT

Method and apparatus for fabricating an oral appliance are described for correcting malocclusions on a dentition of a subject. A three-dimensional representation of the dentition may be captured and a free-form structure having a lattice structure which matches at least part of a surface of the dentition is generated. The lattice structure defines a plurality of open spaces such that the free-form structure is at least partially transparent. The lattice structure may then be manufactured by impregnating or covering a coating into or upon the lattice structure such that the oral appliance is formed.

17 Claims, 9 Drawing Sheets

(56) References Cited

U.S. PATENT DOCUMENTS

| | | | |
|---|---|---|---|
| 6,309,215 B1 | * | 10/2001 | Phan .................... A61C 7/00 433/24 |
| 6,315,553 B1 | | 11/2001 | Sachdeva et al. |
| 6,390,812 B1 | | 5/2002 | Chishti et al. |
| 6,398,548 B1 | | 6/2002 | Chishti et al. |
| 6,454,565 B2 | | 9/2002 | Phan et al. |
| 6,463,344 B1 | | 10/2002 | Pavloskaia |
| 6,471,511 B1 | | 10/2002 | Chishti et al. |
| 6,485,298 B2 | | 11/2002 | Chishti et al. |
| 6,488,499 B1 | | 12/2002 | Miller |
| 6,524,101 B1 | * | 2/2003 | Phan .................... A61C 7/00 433/24 |
| 6,554,611 B2 | | 4/2003 | Chishti et al. |
| 6,572,372 B1 | | 6/2003 | Phan et al. |
| 6,582,227 B2 | | 6/2003 | Phan et al. |
| 6,602,070 B2 | | 8/2003 | Miller et al. |
| 6,607,382 B1 | | 8/2003 | Kuo et al. |
| 6,626,666 B2 | | 9/2003 | Chishti et al. |
| 6,629,840 B2 | | 10/2003 | Chishti et al. |
| 6,682,346 B2 | | 1/2004 | Chishti et al. |
| 6,688,885 B1 | | 2/2004 | Sachdeva |
| 6,699,037 B2 | | 3/2004 | Chishti et al. |
| 6,702,575 B2 | * | 3/2004 | Hilliard ................. A61C 7/00 433/18 |
| 6,705,861 B2 | | 3/2004 | Chishti et al. |
| 6,705,863 B2 | | 3/2004 | Phan et al. |
| 6,722,880 B2 | | 4/2004 | Chishti et al. |
| 6,729,876 B2 | | 5/2004 | Chishti et al. |
| 6,761,560 B2 | | 7/2004 | Miller |
| 6,786,721 B2 | | 9/2004 | Chishti et al. |
| 6,802,713 B1 | | 10/2004 | Chishti et al. |
| 6,830,450 B2 | | 12/2004 | Knopp et al. |
| 6,846,179 B2 | | 1/2005 | Chapouland et al. |
| 6,857,429 B2 | | 2/2005 | Eubank |
| 6,886,566 B2 | | 5/2005 | Eubank |
| 6,964,564 B2 | | 11/2005 | Phan et al. |
| 7,011,517 B2 | | 3/2006 | Nicozisis |
| 7,029,275 B2 | | 4/2006 | Rubbert et al. |
| 7,037,108 B2 | | 5/2006 | Chishti et al. |
| 7,056,115 B2 | | 6/2006 | Phan et al. |
| 7,059,850 B1 | | 6/2006 | Phan et al. |
| 7,063,533 B2 | | 6/2006 | Phan et al. |
| 7,092,784 B1 | | 8/2006 | Simkins |
| 7,104,790 B2 | | 9/2006 | Cronauer |
| 7,121,825 B2 | | 10/2006 | Chishti et al. |
| 7,125,248 B2 | | 10/2006 | Phan et al. |
| 7,134,874 B2 | | 11/2006 | Chishti et al. |
| 7,192,275 B2 | | 3/2007 | Miller |
| 7,320,592 B2 | | 1/2008 | Chishti et al. |
| 7,326,051 B2 | | 2/2008 | Miller |
| 7,331,783 B2 | | 2/2008 | Chishti et al. |
| 7,347,688 B2 | | 3/2008 | Kopelman et al. |
| 7,416,407 B2 | | 8/2008 | Cronauer |
| 7,434,582 B2 | | 10/2008 | Eubank |
| 7,476,100 B2 | | 1/2009 | Kuo |
| 7,553,157 B2 | | 6/2009 | Abolfathi et al. |
| 7,559,328 B2 | | 7/2009 | Eubank |
| 7,578,673 B2 | | 8/2009 | Wen et al. |
| 7,590,462 B2 | | 9/2009 | Rubbert et al. |
| 7,637,262 B2 | | 12/2009 | Bailey |
| 7,641,828 B2 | | 1/2010 | Desimone et al. |
| 7,658,610 B2 | | 2/2010 | Knopp |
| 7,771,195 B2 | | 8/2010 | Knopp et al. |
| 7,802,987 B1 | | 9/2010 | Phan et al. |
| 7,824,180 B2 | | 11/2010 | Abolfathi et al. |
| 7,826,646 B2 | | 11/2010 | Pavlovskaia et al. |
| 7,841,858 B2 | | 11/2010 | Knopp et al. |
| 7,854,609 B2 | | 12/2010 | Chen et al. |
| 7,878,801 B2 | | 2/2011 | Abolfathi et al. |
| 7,878,804 B2 | | 2/2011 | Korytov et al. |
| 7,878,805 B2 | | 2/2011 | Moss et al. |
| 7,883,334 B2 | | 2/2011 | Li et al. |
| 7,901,207 B2 | | 3/2011 | Knopp et al. |
| 7,905,724 B2 | | 3/2011 | Kuo et al. |
| 7,914,283 B2 | | 3/2011 | Kuo |
| 7,942,672 B2 | | 5/2011 | Kuo |
| 7,943,079 B2 | | 5/2011 | Desimone et al. |
| 7,957,824 B2 | | 6/2011 | Boronvinskih et al. |
| 8,001,972 B2 | | 8/2011 | Eubank |
| 8,033,282 B2 | | 10/2011 | Eubank |
| 8,038,444 B2 | | 10/2011 | Kitching et al. |
| 8,070,487 B2 | | 12/2011 | Chishti et al. |
| 8,105,080 B2 | | 1/2012 | Chishti et al. |
| 8,123,519 B2 | | 2/2012 | Schultz |
| 8,152,518 B2 | * | 4/2012 | Kuo .................... A61C 7/08 433/18 |
| 8,235,713 B2 | | 8/2012 | Phan et al. |
| 8,272,866 B2 | | 9/2012 | Chun et al. |
| 8,292,617 B2 | | 10/2012 | Brandt et al. |
| 8,303,302 B2 | | 11/2012 | Teasdale |
| 8,348,665 B2 | | 1/2013 | Kuo |
| 8,356,993 B1 | | 1/2013 | Marston |
| 8,401,686 B2 | | 3/2013 | Moss |
| 8,401,826 B2 | | 3/2013 | Cheng et al. |
| 8,414,412 B2 | | 5/2013 | Baughman et al. |
| 8,439,672 B2 | | 5/2013 | Matov et al. |
| 8,439,673 B2 | | 5/2013 | Korytov et al. |
| 8,469,706 B2 | | 6/2013 | Kuo |
| 8,496,474 B2 | | 7/2013 | Chishti et al. |
| 8,517,726 B2 | | 8/2013 | Kakavand et al. |
| 8,535,580 B2 | | 9/2013 | Puttler et al. |
| 8,562,337 B2 | | 10/2013 | Kuo et al. |
| 8,562,340 B2 | | 10/2013 | Chishti et al. |
| 8,690,568 B2 | | 4/2014 | Chapoulaud et al. |
| 8,708,697 B2 | | 4/2014 | Li et al. |
| 8,734,149 B2 | | 5/2014 | Phan et al. |
| 8,734,150 B2 | | 5/2014 | Chishti et al. |
| 8,738,165 B2 | | 5/2014 | Cinader, Jr. et al. |
| 8,765,031 B2 | | 7/2014 | Li et al. |
| 8,777,611 B2 | | 7/2014 | Cios |
| 8,780,106 B2 | | 7/2014 | Chishti et al. |
| 8,807,999 B2 | | 8/2014 | Kuo et al. |
| 8,858,226 B2 | | 10/2014 | Phan et al. |
| 8,864,493 B2 | | 10/2014 | Leslie-Martin et al. |
| 8,899,976 B2 | | 12/2014 | Chen et al. |
| 8,936,464 B2 | | 1/2015 | Kopelman |
| 8,944,812 B2 | | 2/2015 | Kuo |
| 8,961,173 B2 | | 2/2015 | Miller |
| 8,986,003 B2 | | 3/2015 | Valoir |
| 8,992,215 B2 | | 3/2015 | Chapoulaud et al. |
| 9,004,915 B2 | | 4/2015 | Moss et al. |
| 9,022,781 B2 | | 5/2015 | Kuo et al. |
| 9,026,238 B2 | | 5/2015 | Kraemer et al. |
| 9,060,829 B2 | | 6/2015 | Sterental et al. |
| 9,107,722 B2 | | 8/2015 | Matov et al. |
| 9,119,691 B2 | | 9/2015 | Namiranian et al. |
| 9,161,823 B2 | | 10/2015 | Morton et al. |
| 9,161,824 B2 | | 10/2015 | Chishti et al. |
| 9,204,942 B2 | | 12/2015 | Phan et al. |
| 9,241,774 B2 | | 1/2016 | Li et al. |
| 9,301,814 B2 | | 4/2016 | Kaza et al. |
| 9,320,575 B2 | | 4/2016 | Chishti et al. |
| 9,333,052 B2 | | 5/2016 | Miller |
| 9,345,557 B2 | | 5/2016 | Anderson |
| 9,351,809 B2 | | 5/2016 | Phan et al. |
| 9,375,300 B2 | | 6/2016 | Matov et al. |
| 2002/0010568 A1 | | 1/2002 | Rubbert et al. |
| 2002/0025503 A1 | | 2/2002 | Chapoulaud et al. |
| 2002/0094503 A1 | | 7/2002 | Chishti et al. |
| 2003/0008259 A1 | | 1/2003 | Kuo et al. |
| 2003/0190576 A1 | | 10/2003 | Phan et al. |
| 2004/0152036 A1 | | 8/2004 | Abolfathi |
| 2004/0166456 A1 | | 8/2004 | Chishti et al. |
| 2004/0166462 A1 | | 8/2004 | Phan et al. |
| 2004/0166463 A1 | | 8/2004 | Wen et al. |
| 2004/0197728 A1 | | 10/2004 | Abolfathi et al. |
| 2004/0202983 A1 | | 10/2004 | Tricca et al. |
| 2005/0010450 A1 | | 1/2005 | Hultgren et al. |
| 2005/0153255 A1 | | 7/2005 | Sporbert et al. |
| 2005/0244782 A1 | | 11/2005 | Chishti et al. |
| 2006/0003283 A1 | | 1/2006 | Miller et al. |
| 2006/0035197 A1 | | 2/2006 | Hishimoto |
| 2006/0068353 A1 | * | 3/2006 | Abolfathi ................ A61C 7/00 433/6 |

(56) References Cited

U.S. PATENT DOCUMENTS

| | | |
|---|---|---|
| 2006/0078840 A1 | 4/2006 | Robson |
| 2006/0078841 A1 | 4/2006 | Desimone et al. |
| 2006/0093982 A1 | 5/2006 | Wen |
| 2006/0099546 A1 | 5/2006 | Bergersen |
| 2006/0115785 A1 | 6/2006 | Li et al. |
| 2006/0177789 A1 | 8/2006 | O'Bryan |
| 2006/0188834 A1 | 8/2006 | Hilliard |
| 2006/0199142 A1 | 9/2006 | Liu et al. |
| 2006/0223022 A1 | 10/2006 | Solomon |
| 2006/0223023 A1 | 10/2006 | Lai et al. |
| 2006/0275731 A1 | 12/2006 | Wen et al. |
| 2007/0003907 A1 | 1/2007 | Chishti et al. |
| 2007/0283967 A1 | 12/2007 | Bailey |
| 2008/0032248 A1 | 2/2008 | Kuo |
| 2008/0044786 A1 | 2/2008 | Kalili |
| 2008/0050692 A1 | 2/2008 | Hilliard |
| 2008/0051650 A1 | 2/2008 | Massie et al. |
| 2008/0057462 A1 | 3/2008 | Kitching et al. |
| 2008/0076086 A1 | 3/2008 | Kitching et al. |
| 2008/0085487 A1 | 4/2008 | Kuo et al. |
| 2008/0118882 A1 | 5/2008 | Su |
| 2008/0141534 A1 | 6/2008 | Hilliard |
| 2008/0182220 A1 | 7/2008 | Chishti et al. |
| 2008/0206702 A1 | 8/2008 | Hedge et al. |
| 2008/0215176 A1 | 9/2008 | Borovinskih et al. |
| 2008/0248438 A1 | 10/2008 | Desimone et al. |
| 2008/0248443 A1 | 10/2008 | Chisti et al. |
| 2008/0261165 A1 | 10/2008 | Steingart et al. |
| 2008/0268400 A1 | 10/2008 | Moss et al. |
| 2009/0081604 A1 | 3/2009 | Fisher |
| 2009/0191502 A1 | 7/2009 | Cao et al. |
| 2009/0269714 A1 | 10/2009 | Knopp |
| 2009/0280450 A1 | 11/2009 | Kuo |
| 2009/0291407 A1 | 11/2009 | Kuo |
| 2009/0291408 A1 | 11/2009 | Stone-Collonge et al. |
| 2010/0055635 A1 | 3/2010 | Kakavand |
| 2010/0167225 A1 | 7/2010 | Kuo |
| 2010/0280798 A1 | 11/2010 | Pattijn et al. |
| 2011/0005527 A1 | 1/2011 | Andrew et al. |
| 2011/0015591 A1 | 1/2011 | Hanson et al. |
| 2011/0020761 A1 | 1/2011 | Kalili |
| 2011/0039223 A1* | 2/2011 | Li .................. A61C 7/08 433/6 |
| 2011/0114100 A1 | 5/2011 | Alvarez et al. |
| 2011/0123944 A1 | 5/2011 | Knopp et al. |
| 2011/0129786 A1 | 6/2011 | Chun et al. |
| 2011/0165533 A1 | 7/2011 | Li et al. |
| 2011/0269092 A1 | 11/2011 | Kuo et al. |
| 2011/0281229 A1 | 11/2011 | Abolfathi |
| 2012/0123577 A1 | 5/2012 | Chapoulaud et al. |
| 2012/0150494 A1 | 6/2012 | Anderson et al. |
| 2012/0186589 A1 | 7/2012 | Singh |
| 2012/0199136 A1 | 8/2012 | Urbano |
| 2012/0214121 A1 | 8/2012 | Greenberg |
| 2012/0225399 A1 | 9/2012 | Teasdale |
| 2012/0225400 A1 | 9/2012 | Chishti et al. |
| 2012/0244488 A1 | 9/2012 | Chishti et al. |
| 2012/0270173 A1 | 10/2012 | Pumphrey et al. |
| 2012/0288818 A1 | 11/2012 | Vendittelli |
| 2013/0052625 A1 | 2/2013 | Wagner |
| 2013/0078593 A1* | 3/2013 | Andreiko ............ A61C 7/08 433/6 |
| 2013/0081271 A1 | 4/2013 | Farzin-Nia et al. |
| 2013/0095446 A1 | 4/2013 | Andreiko et al. |
| 2013/0122445 A1 | 5/2013 | Marston |
| 2013/0122448 A1 | 5/2013 | Kitching |
| 2013/0157213 A1 | 6/2013 | Arruda |
| 2013/0201450 A1 | 8/2013 | Bailey et al. |
| 2013/0204583 A1 | 8/2013 | Matov et al. |
| 2013/0230819 A1 | 9/2013 | Arruda |
| 2013/0236848 A1 | 9/2013 | Arruda |
| 2013/0266906 A1 | 10/2013 | Soo |
| 2013/0302742 A1 | 11/2013 | Li et al. |
| 2013/0323665 A1 | 12/2013 | Dinh et al. |
| 2013/0325431 A1 | 12/2013 | See et al. |
| 2014/0072926 A1 | 3/2014 | Valoir |
| 2014/0076332 A1 | 3/2014 | Luco |
| 2014/0124968 A1 | 5/2014 | Kim |
| 2014/0172375 A1 | 6/2014 | Grove |
| 2014/0193767 A1 | 7/2014 | Li et al. |
| 2014/0229878 A1 | 8/2014 | Wen et al. |
| 2014/0242532 A1 | 8/2014 | Arruda |
| 2014/0272757 A1 | 9/2014 | Chishti |
| 2014/0287376 A1 | 9/2014 | Hultgren et al. |
| 2014/0288894 A1 | 9/2014 | Chishti et al. |
| 2014/0315153 A1 | 10/2014 | Kitching |
| 2014/0315154 A1 | 10/2014 | Jung et al. |
| 2014/0067335 A1 | 11/2014 | Andreiko |
| 2014/0329194 A1 | 11/2014 | Sachdeva et al. |
| 2014/0349242 A1 | 11/2014 | Phan et al. |
| 2014/0363779 A1 | 12/2014 | Kopelman |
| 2014/0370452 A1 | 12/2014 | Tseng |
| 2015/0004553 A1 | 1/2015 | Li et al. |
| 2015/0004554 A1 | 1/2015 | Cao et al. |
| 2015/0018956 A1 | 1/2015 | Steinmann et al. |
| 2015/0044623 A1 | 2/2015 | Rundlett |
| 2015/0044627 A1 | 2/2015 | German |
| 2015/0093713 A1 | 4/2015 | Chen et al. |
| 2015/0093714 A1 | 4/2015 | Kopelman |
| 2015/0125802 A1 | 5/2015 | Tal |
| 2015/0128421 A1 | 5/2015 | Mason et al. |
| 2015/0157421 A1 | 6/2015 | Martz et al. |
| 2015/0182321 A1 | 7/2015 | Karazivan et al. |
| 2015/0216626 A1 | 8/2015 | Ranjbar |
| 2015/0216627 A1 | 8/2015 | Kopelman |
| 2015/0238282 A1 | 8/2015 | Kuo et al. |
| 2015/0238283 A1 | 8/2015 | Tanugula |
| 2015/0238284 A1 | 8/2015 | Wu et al. |
| 2015/0245887 A1 | 9/2015 | Izugami et al. |
| 2015/0254410 A1 | 9/2015 | Sterental et al. |
| 2015/0265376 A1 | 9/2015 | Kopelman |
| 2015/0289949 A1 | 10/2015 | Moss et al. |
| 2015/0289950 A1 | 10/2015 | Khan |
| 2015/0305830 A1 | 10/2015 | Howard et al. |
| 2015/0320518 A1 | 11/2015 | Namiranian et al. |
| 2015/0320532 A1 | 11/2015 | Matty et al. |
| 2015/0335399 A1 | 11/2015 | Caraballo |
| 2015/0335404 A1 | 11/2015 | Webber et al. |
| 2015/0336299 A1 | 11/2015 | Tanugula |
| 2015/0342464 A1 | 12/2015 | Wundrak et al. |
| 2015/0351871 A1 | 12/2015 | Chishti et al. |
| 2015/0359609 A1 | 12/2015 | Khan |
| 2015/0366637 A1 | 12/2015 | Kopelman et al. |
| 2015/0366638 A1 | 12/2015 | Kopelman et al. |
| 2016/0000527 A1 | 1/2016 | Arruda |
| 2016/0008095 A1 | 1/2016 | Matov et al. |
| 2016/0008097 A1 | 1/2016 | Chen et al. |
| 2016/0051341 A1 | 2/2016 | Webber |
| 2016/0051342 A1 | 2/2016 | Phan et al. |
| 2016/0051348 A1 | 2/2016 | Boerjes et al. |
| 2016/0067013 A1 | 3/2016 | Morton et al. |
| 2016/0067014 A1 | 3/2016 | Kottemann et al. |
| 2016/0074137 A1 | 3/2016 | Kuo et al. |
| 2016/0106521 A1 | 4/2016 | Tanugula |
| 2016/0120617 A1 | 5/2016 | Lee |
| 2016/0120621 A1 | 5/2016 | Li et al. |
| 2016/0128803 A1 | 5/2016 | Webber et al. |
| 2016/0135924 A1 | 5/2016 | Choi et al. |
| 2016/0135926 A1 | 5/2016 | Djamchidi |
| 2016/0135935 A1 | 5/2016 | Boltunov et al. |
| 2016/0157961 A1 | 6/2016 | Lee |
| 2016/0175068 A1 | 6/2016 | Cai et al. |
| 2016/0175069 A1 | 6/2016 | Korytov et al. |
| 2016/0184129 A1 | 6/2016 | Liptak et al. |
| 2016/0193014 A1 | 7/2016 | Morton et al. |
| 2016/0256240 A1 | 9/2016 | Shivapuja et al. |
| 2017/0100207 A1 | 4/2017 | Wen |
| 2017/0100208 A1 | 4/2017 | Wen |
| 2017/0100210 A1 | 4/2017 | Wen |
| 2017/0100211 A1 | 4/2017 | Wen |
| 2017/0100214 A1 | 4/2017 | Wen |
| 2018/0014912 A1* | 1/2018 | Radmand ............ A61C 5/007 |
| 2018/0078335 A1 | 3/2018 | Falkel |

(56) References Cited

U.S. PATENT DOCUMENTS

| | | |
|---|---|---|
| 2018/0078343 A1 | 3/2018 | Falkel |
| 2018/0078344 A1 | 3/2018 | Falkel |
| 2018/0078347 A1 | 3/2018 | Falkel |

FOREIGN PATENT DOCUMENTS

| | | |
|---|---|---|
| WO | WO 2009/068892 | 6/2009 |
| WO | WO 2016/004415 | 1/2016 |
| WO | WO 2017/062207 | 4/2017 |
| WO | WO 2017/062208 | 4/2017 |
| WO | WO 2017/062209 | 4/2017 |
| WO | WO 2017/062210 | 4/2017 |
| WO | WO 2018/057622 | 3/2018 |
| WO | WO 2018/118200 | 6/2018 |

\* cited by examiner

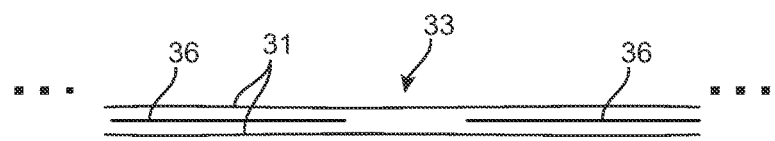
FIG. 2D
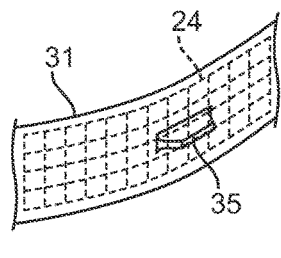 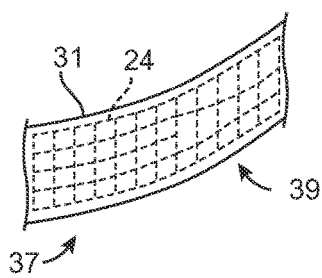 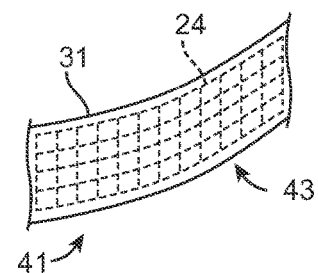
FIG. 2E            FIG. 2F            FIG. 2G
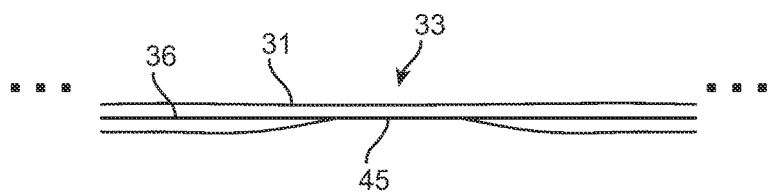
FIG. 2H

THREE-DIMENSIONAL PRINTED DENTAL APPLIANCES USING LATTICES

CROSS-REFERENCE TO RELATED APPLICATIONS

This application claims the benefit of priority to U.S. Provisional Application No. 62/238,532 filed Oct. 7, 2015, which is incorporated herein by reference in its entirety.

FIELD OF THE INVENTION

The present invention relates to methods and apparatus for the fabrication of dental appliances such as retainers and aligners using three-dimensional (3D) printing processes. More particularly, the present invention relates to methods and apparatus for fabricating dental appliance using three-dimensional (3D) printing processes where the appliances may be formed to have hollow shapes with complex geometries using tiny cell lattice structures.

BACKGROUND OF THE INVENTION

Orthodontics is a specialty of dentistry that is concerned with the study and treatment of malocclusion, which can be a result of tooth irregularity, disproportionate facial skeleton relationship, or both. Orthodontics treats malocclusion through the displacement of teeth via bony remodeling and control and modification of facial growth.

This process has been traditionally accomplished by using static mechanical force to induce bone remodeling, thereby enabling teeth to move. In this approach, braces consisting of an archwire interfaces with brackets that are affixed to each tooth. As the teeth respond to the pressure applied via the archwire by shifting their positions, the wires are again tightened to apply additional pressure. This widely accepted approach to treating malocclusion takes about twenty-four months on average to complete, and is used to treat a number of different classifications of clinical malocclusion. Treatment with braces is complicated by the fact that it is uncomfortable and/or painful for patients, and the orthodontic appliances are perceived as unaesthetic, all of which creates considerable resistance to use. Further, the treatment time cannot be shortened by increasing the force, because too high a force results in root resorption, as well as being more painful. The average treatment time of 24-months is very long, and further reduces usage. In fact, some estimates provide that less than half of the patients who could benefit from such treatment elect to pursue orthodontics.

Kesling introduced the tooth positioning appliance in 1945 as a method of refining the final stage of orthodontic finishing after removal of the braces (de-banding). The positioner was a one-piece pliable rubber appliance fabricated on the idealized wax set-ups for patients whose basic treatment was complete. Kesling also predicted that certain major tooth movements could also be accomplished with a series of positioners fabricated from sequential tooth movements on the set-up as the treatment progressed. However, this idea did not become practical until the advent of three-dimensional (3D) scanning and computer and used by Align Technologies and others such as OrthoClear, Clear-Aligner and ClearCorrect to provide greatly improved aesthetics since the devices are transparent.

SUMMARY OF THE INVENTION

The present invention relates to free-form structures fitting the surface of a body part. In particular embodiments, the free-form structures include oral appliances or aligners, although the devices and methods described are not so limited.

One method for fabricating an oral appliance may generally comprise capturing a three-dimensional representation of a dentition of a subject and generating a free-form structure having a lattice structure which matches at least part of a surface of the dentition, wherein the lattice structure defines a plurality of open spaces such that the free-form structure is at least partially transparent. The lattice structure may then be manufactured by impregnating or covering a coating into or upon the lattice structure such that the oral appliance is formed.

One or more oral appliances may thus be manufactured where each subsequent oral appliance is configured to impart a movement of one or more teeth of the subject and is intended to be worn by the subject to correct for any malocclusions.

Generally, the oral appliance may comprise the lattice structure which is configured to match at least part of a surface of a dentition of the subject, wherein the lattice structure defines a plurality of open spaces such that the free-form structure is at least partially transparent. A coating may impregnate or cover into or upon the lattice structure and at least one dental attachment structure may be formed as part of the lattice structure, wherein the dental attachment structure is located in proximity to one or more teeth to be moved.

The system provides free-form structures fitting the surface of a body part, which are at least partially made by additive manufacturing. The free-form structures may comprise a basic structure which includes a lattice structure and a coating material provided thereon. The lattice structure may be impregnated in and/or enclosed by the coating material which may include, e.g., polymeric or ceramic materials and metals. Furthermore, the coating material may include different regions of varying thickness or other features incorporated into the material. The polymer may include a number of different types, e.g., silicone, polyurethane, polyepoxide, polyamides, or blends thereof, etc. In alternative embodiments, the lattice structure may be impregnated in and/or enclosed by a foamed solid.

In certain embodiments, the lattice structure may be defined by a plurality of unit cells with a size between, e.g., 1 and 20 mm. In other embodiments, the lattice structure may be provided with varying unit, cell geometries having cell varying dimensions and/or varying structure densities. In other embodiments, the lattice structure may be comprised of at least two separate lattice structure parts movably connected to each other and integrated into the structure.

In certain embodiments, the free-form structure may further include one or more external and/or internal sensors (e.g. pressure and/or temperature sensors) and/or one or more external and/or internal markers (e.g. position markers). Such markers can be read externally to determine current tooth movement to help the practitioner in deciding future movement adjustments, if needed.

In certain embodiments, the free-form structure may further include one or more agents disposed externally and/or internally such as various chemicals or drugs, e.g., tooth whitening materials, insulin which can be slowly delivered orally to a diabetic patient, etc. Such chemicals, drugs, or medicine can also be incorporated to loosen up the gums and/or tendons to enable teeth move faster, wound treatments, etc.

In certain embodiments, the free-form structure may further comprise one or more external and/or internal locators so that, when such a device is misplaced, the user can use a mobile computer to detect the location and find the device. The locator can include any number of devices, e.g., magnets, wireless proximity detectors, optical proximity detectors, etc.

The free-form structures can also be further configured to have different stiffness values in different regions of the structure utilizing a number of different configurations.

BRIEF DESCRIPTION OF THE DRAWINGS

The following description of the figures of specific embodiments of the invention, is merely exemplary in nature and is not intended to limit the present teachings, their application or uses. Throughout the drawings, corresponding reference numerals indicate like or corresponding parts and features.

FIG. 2D shows an exemplary end view of a lattice structure having regions comprised only of the coating material.

FIG. 2E shows a detail perspective view of a lattice structure and coating having a feature such as an extension formed from the surface.

FIG. 2F shows a detail perspective view of a lattice structure and coating having different regions with varying unit cell geometries.

FIG. 2G shows a detail perspective view of a lattice structure and coating having different regions formed with different thicknesses.

FIG. 2H shows an exemplary end view of a lattice structure having regions with a coating on a single side.

DETAILED DESCRIPTION OF THE INVENTION

Figure 1A:
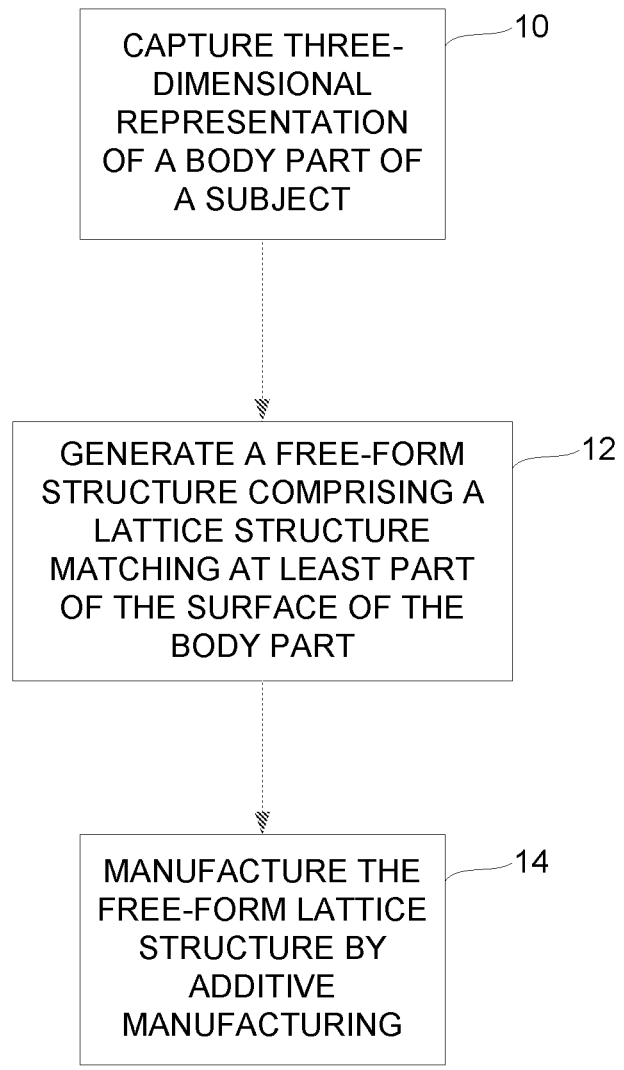
FIG. 1A shows an exemplary process for fabricating a dental appliance using a lattice structure.

The present invention will be described with respect to particular embodiments but the invention is not limited thereto but only by the claims. Any reference signs in the claims shall not be construed as limiting the scope thereof.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" when referring to recited members, elements or method steps also include embodiments which "consist of" said recited members, elements or method steps.

Furthermore, the terms first, second, third and the like in the description and in the claims, are used for distinguishing between similar elements and not necessarily for describing a sequential or chronological order, unless specified. It is to be understood that the terms so used are interchangeable under appropriate circumstances and that the embodiments of the invention described herein are capable of operation in other sequences than described or illustrated herein.

The term "about" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

The recitation of numerical ranges by endpoints includes all numbers and fractions subsumed within the respective ranges, as well as the recited endpoints.

All documents cited in the present specification are hereby incorporated by reference in their entirety.

Unless otherwise defined, all terms used in disclosing the invention, including technical and scientific terms, have the meaning as commonly understood by one of ordinary skill in the art to which this invention belongs. By means of further guidance, definitions for the terms used in the description are included to better appreciate the teaching of the present invention. The terms or definitions used herein are provided solely to aid in the understanding of the invention.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

The system described herein is related to the fabrication of dental appliances such as retainers and aligners using three-dimensional (3D) printing processes. The appliance may be formed to have hollow shapes with complex geometries using tiny cells known as lattice structures. Topology optimization can be used to assist in the efficient blending of solid-lattice structures with smooth transitional material volume. Lattice performance can be studied under tension, compression, shear, flexion, torsion, and fatigue life.

Free-form lattice structures are provided herein, which fit at least part of the surface, e.g. external contour, of a body part. Specifically, the embodiments described may utilize free-form lattice structures for forming, or fabricating appliances which are designed for placement or positioning upon the external surfaces of a patient's dentition for correcting one or more malocclusions. The free-form structure is at least partially fabricated by additive manufacturing techniques and utilizes a basic structure comprised of a lattice structure. The lattice structure may ensure and/or contribute to a free-form structure having a defined rigidity and the lattice structure may also ensure optimal coverage on the dentition by a coating material which may be provided on the lattice structure. The lattice structure is at least partly covered by, impregnated in, and/or enclosed by the coating material. Furthermore, embodiments of the lattice structure can contribute to the transparency of the structure.

The term "free-form lattice structure", as used herein, refers to a structure having an irregular and/or asymmetrical flowing shape or contour, more particularly fitting at least part of the contour of one or more body parts. Thus, in particular embodiments, the free-form structure may be a free-form surface. A free-form surface refers to an (essentially) two-dimensional shape contained in a three-dimensional geometric space. Indeed, as detailed herein, such a surface can be considered as essentially two-dimensional in that it has limited thickness, but may nevertheless to some degree have a varying thickness. As it comprises a lattice structure rigidly set to mimic a certain shape it forms a three-dimensional structure.

Typically, the free-form structure or surface is characterized by a lack of corresponding radial dimensions, unlike regular surfaces such as planes, cylinders and conic surfaces. Free-form surfaces are known to the skilled person and widely used in engineering design disciplines. Typically non-uniform rational B-spline (NURBS) mathematics is used to describe the surface forms; however, there are other methods such as Gorden surfaces or Coons surfaces. The form of the free-form surfaces are characterized and defined not in terms of polynomial equations, but by their poles, degree, and number of patches (segments with spline curves). Free-form surfaces can also be defined as triangulated surfaces, where triangles are used to approximate the 3D surfaces. Triangulated surfaces are used in Standard Triangulation Language (STL) files which are known to a person skilled in CAD design. The free-form structures fit the surface of a body part, as a result of the presence of a rigid basic structures therein, which provide the structures their free-form characteristics.

The term "rigid" when referring to the lattice structure and/or free-form structures comprising them herein refers to a structure showing a limited degree of flexibility, more particularly, the rigidity ensures that the structure forms and retains a predefined shape in a three-dimensional space prior to, during and after use and that this overall shape is mechanically and/or physically resistant to pressure applied thereto. In particular embodiments the structure is not foldable upon itself without substantially losing its mechanical integrity, either manually or mechanically. Despite the overall rigidity of the shape of the envisaged structures, the specific stiffness of the structures may be determined by the structure and/or material of the lattice structure. Indeed, it is envisaged that the lattice structures and/or free-form structures, while maintaining their overall shape in a three-dimensional space, may have some (local) flexibility for handling. As will be detailed herein, (local) variations can be ensued by the nature of the pattern of the lattice structure, the thickness of the lattice structure and the nature of the material. Moreover, as will be detailed below, where the free-form structures envisaged herein comprise separate parts (e.g. non-continuous lattice structures) which are interconnected (e.g., by hinges or by areas of coating material), the rigidity of the shape may be limited to each of the areas comprising a lattice structure.

Generally, the methods envisaged herein are for dental appliance fabrication processes where the fabrication process includes designing an appliance worn on teeth to be covered by a free-form structure, manufacturing the mold, and providing the (one or more) lattice structures therein and providing the coating material in the mold so as to form the free-form structure. The free-form structures are patient-specific, i.e. they are made to fit specifically on the anatomy or dentition of a certain patient, e.g., animal or human. FIG. 1A generally shows an overall exemplary method for fabricating a dental appliance by capturing a 3D representation of a body part of a subject 10. In this example, this may involve capturing the 3D representation of the surfaces, e.g. external contours, of a patient's dentition for correcting one or more malocclusions. For this purpose, the subject may be scanned using a 3D scanner, e.g. a hand-held laser scanner, and the collected data can then be used to construct a digital, three dimensional model of the body part of the subject. Alternatively, the patient-specific images can be provided by a technician or medical practitioner by scanning the subject or part thereof. Such images can then be used as or converted into a three-dimensional representation of the subject, or part thereof. Additional steps wherein the scanned image is manipulated and for instance cleaned up may be envisaged.

With the captured 3D representation, a free-form structure comprised generally of a lattice structure matching at least part of the surface of the body part, e.g., dentition, may be generated 12. Designing a free-form structure based on said three dimensional representation of said body part, such that the structure is essentially complementary to at least part of said body part and comprises or consists of a lattice structure. In the lattice structure, one or more types and/or sizes of unit cell may be selected, depending on the subject shape, the required stiffness of the free-form structure, etc. Different lattice structures may be designed within the free-form structure for fitting on different locations on the body part. The different lattice structures may be provided with, e.g., a hinge or other movable mechanism, so that they can be connected and/or, can be digitally blended together or connected by beams in the basic structure to form a single part.

This step may also include steps required for designing the lattice structure, including for instances of defining surfaces on the positive print of the mask that may need different properties, different cell sizes and/or openings, generating the cells with the required geometry and patterning them as needed on the defined surfaces to cover said surfaces, and combining the separate cell patterns into a single solid part. It should be noted that the requirements of the lattice structure would be clear to a skilled person while designing the lattice structure. The skilled person will therefore use data obtained from his own experience as well as data from numerical modeling systems, such as FE and/or CFD models.

The free-form lattice structure may then be actually manufactured, e.g., by additive manufacturing methods 14. In certain embodiments, this may include providing a coating material on the basic structure in which coating material is preferably a polymer. These different steps need not be performed in the same location or by the same actors. Indeed typically, the design of the free-form structure, the manufacturing and the coating may be accomplished in different locations by different actors. Moreover, it is envisaged that additional steps may be performed between the steps recited above. In coating or impregnating the free-form basic structure, the lattice structure may be impregnated with a certain material, such as a polymer, thereby generating the free-form structure. This may include steps such as adding the polymeric material or other material into the dental appliance, curing the material impregnating the lattice structure and disassembling the dental appliance.

After manufacturing the free-form structure, the structure may go through a number of post-process steps including for instance cleaning up and finishing the free-form structure. Moreover, other applications of forming a rigid free-form structure as described herein may also include applications for, but not limited to, therapeutic, cosmetic and protective applications.

In one particular application, the use of the free-form structures described herein may be used in the care and treatment of damaged skin surfaces, such as burn wounds. In further embodiments, the use of the free-from structures described herein may be used in the care, protection, and treatment of undamaged skin surfaces. According to additional particular embodiments, the use of a free-form structure as described herein may be used for cosmetic purposes. In further embodiments, the use of a free-form structure as described herein may be used for the delivery of treatment agents to the skin. In other particular embodiments, the structure further comprises one or more therapeutic compositions which may be embedded in the coating material. In yet further embodiments, the use of the structures described herein may be used as prosthetic devices, e.g., for replacing a body part, where the free-forms structure may be made to be identical to the missing body part.

Figure 1B:
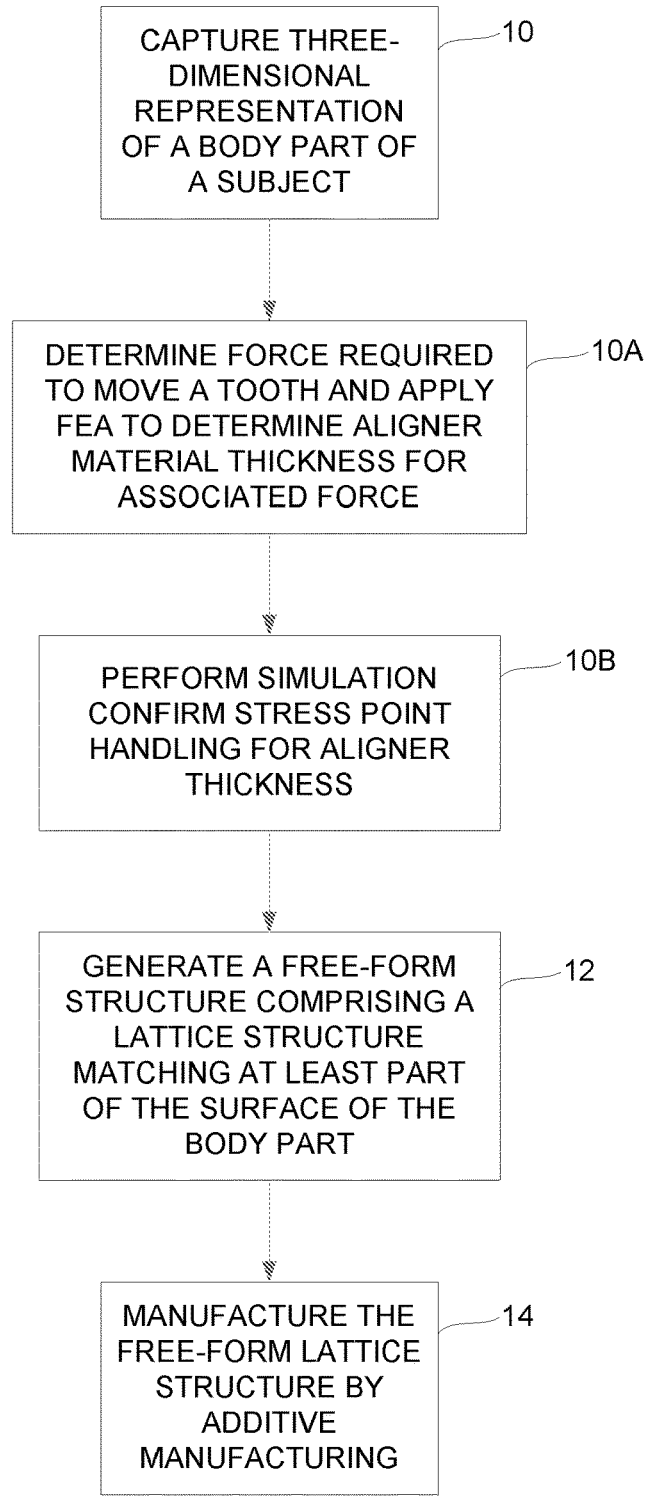
FIG. 1B shows an exemplary process for fabricating a dental appliance with varying material thickness using a lattice structure.

FIG. 1B shows another overall exemplary process for fabricating a dental appliance having a lattice structure similarly to that shown above in FIG. 1A. In this example, once the 3D representation has been captured 10, the amount of force required to move a tooth or teeth may be determined and finite element analysis may be utilized to determine an appropriate thickness of aligner material needed for the associated force 10A to move a particular tooth or teeth. In this manner, one or more oral appliances may be fabricated with varying material thicknesses in which regions which may not require much force are fabricated to have a relatively thinner region while regions of the appliance which may require a greater amount of force to move the tooth or teeth may be fabricated to have relatively thicker regions of material to create an oral appliance having directional strength (Differential Force) depending on the particular forces needed to correct particular malocclusions. Simulations may be performed on the modeled dentition (or aligners) to confirm stress point handling for the various aligner thicknesses 10B.

Then as previously described, a free-form structure comprised generally of a lattice structure matching at least part of the surface of the body part, e.g., dentition, may be generated 12 and the free-form lattice structure may then be actually manufactured, e.g., by additive manufacturing methods 14. However, the one or more oral appliances may be fabricated to have regions of relatively thickened and/or thinned material to accommodate the directional strength (Differential Force) of the oral appliances, as described in further detail below.

FIG. 2 shows a perspective view of an exemplary oral appliance 20 having two parts 22 (for the upper dentition and lower dentition). As shown, the oral appliance 20 generally includes a lattice structure 24 which can be used in a process for manufacturing the final oral appliance. In the process, the lattice structure 24 may first be 3D printed in a shape which approximates the oral appliance to be fabricated for correcting the malocclusion and the lattice structure may be positioned within a dental appliance 26, 26'. Then, the dental appliance 26, 26' containing the formed lattice structure 24 may be filled with the impregnating material 28, e.g., polymer or other materials described herein. After setting of the impregnating material 28, the dental appliance halves 26, 26' are removed to yield the coated oral appliance 20.

While the entire lattice structure 24 may be coated or impregnated by the impregnating material 28, only portions of the lattice structure 24 may be coated or particular surfaces of the lattice structure 24 may be coated while leaving other portions exposed. Variations of these embodiments are described in further detail below with respect to the oral appliance 20 shown in FIG. 2.

As can be appreciated, an approach to 3D printed progressive aligners of varying and/or increasing thickness has certain advantages. For example, the rate of incremental increase in thickness may not be dependent on standard thicknesses of sheet plastic available as an industrial commodity. An optimal thickness could be established for the 3D printing process. For example, rather than being limited to the, e.g., 0.040, 0.060 and 0.080 in, thickness sequence, a practitioner such as an orthodontist could choose a sequence such as, e.g., 0.040, 0.053 and 0.066 in, thickness, for an adult patient whose teeth are known to reposition more slowly compared to a rapidly growing adolescent patient.

Given the concept that an aligner formed from thinner material generates generally lower corrective forces than an identically configured aligner formed from thicker material, it follows that an aligner could be 3D printed so as to be thicker in areas where higher forces are needed and thinner in areas where lighter forces are needed. Having the latitude to produce aligners with first a default thickness and then areas of variable thickness could be favorably exploited to help practitioners address many difficult day-to-day challenges. For example, any malocclusion will consist of teeth that are further from their desired finished positions than other teeth. Further, some teeth are smaller than others and the size of the tooth corresponds to the absolute force threshold needed to initiate tooth movement. Other teeth may seem to be more stubborn due to many factors including the proximity of the tooth's root to the boundaries between cortical and alveolar bony support. Still other teeth are simply harder to correctively rotate, angulate, or up-right than others. Still other teeth and groups of teeth may need to be bodily moved as rapidly as possible over comparatively large spans to close open spaces. For at least such reasons, the option of tailoring aligner thickness and thus force levels around regions containing larger teeth or teeth that are further from their desired destinations, or those stubborn teeth allows those selected teeth to receive higher forces than small, nearly ideally positioned teeth.

The free-form lattice structure for the dental appliances can be at least partially fabricated by additive manufacturing, (AM). More particularly, at least the basic structure may be fabricated by additive manufacturing using the lattice structure. Generally, AM can may include a group of techniques used to fabricate a tangible model of an object typically using 3D computer aided design (CAD) data of the object. A multitude of AM techniques are available for use, e.g., stereolithography, selective laser sintering, fused deposition modeling, foil-based techniques, etc. Selective laser sintering uses a high power laser or another focused heat source to sinter or weld small particles of plastic, metal, or ceramic powders into a mass representing the 3D object to be formed. Fused deposition modeling and related techniques make use of a temporary transition from a solid material to a liquid state, usually due to heating. The material is driven through an extrusion nozzle in a controlled way and deposited in the required place as described among others in U.S. Pat. No. 5,141,680, which is incorporated herein by reference in its entirety and for any purpose. Foil-based techniques fix coats to one another by use of, e.g., gluing or photo polymerization or other techniques, and then cuts the object from these coats or polymerize the object. Such a technique is described in U.S. Pat. No. 5,192,539, which is incorporated herein by reference in its entirety and for any purpose.

Typically AM techniques start from a digital representation of the 3D object to be formed. Generally, the digital representation is sliced into a series of cross-sectional layers which can be overlaid to form the object as a whole. The AM apparatus uses this data for building the object on a layer-by-layer basis. The cross-sectional data representing the layer data of the 3D object may be generated using a computer system and computer aided design and manufacturing (CAD/CAM) software.

The basic structure comprising the lattice structure may thus be made of any material which is compatible with additive manufacturing and which is able to provide a sufficient stiffness to the rigid shape of the regions comprising the lattice structure in the free-form structure or the free-form structure as a whole. Suitable materials include, but are not limited to, e.g., polyurethane, acrylonitrile butadiene styrene (ABS), polycarbonate (PC), PC-ABS, polyamide, polyamide with additives such as glass or metal particles, methyl methacrylate-acrylonitrile-butadiene-styrene copolymer, etc.

The lattice structure itself may be comprised of a rigid structure which has an open framework of, e.g., 3D printed lattices. Lattice structures may contain a plurality of lattices cells, e.g., dozens, thousands, hundreds of thousands, etc. lattice cells. Once the 3D model of the dentition is provided, the process may generate STL files to print the lattice version of the 3D model and create support structures where necessary. The system identifies where material is needed in an appliance and where it is not required, prior to placing and optimizing the lattice.

The system may optimize dental lattices in two phases. First, it applies a topology optimization allowing more porous materials with intermediate densities to exist. Second, the porous zones are transformed into explicit lattice structures with varying material volume. In the second phase, the dimensions of the lattice cells are optimized. The result is a structure with solid parts plus lattice zones with varying volumes of material. The system balances the relationship between material density and part performance, for example, with respect to the stiffness to volume ratio, that can impact design choices made early in the product development process. Porosity may be especially important as a functional requirement for biomedical implants. Lattice zones could be important to the successful development of products where more than mere stiffness is required. The system can consider buckling behavior, thermal performance, dynamic characteristics, and other aspects, all of which can be optimized. The user may manipulate material density based upon the result of an optimization process, comparing stronger versus weaker, or solid versus void versus lattice, designs. The designer first defines the objective, then performs optimization analysis to inform the design.

While 3D printing may be used, the lattices can also be made of strips, bars, girders, beams or the like, which are contacting, crossing or overlapping in a regular pattern. The strips, bars, girders, beams or the like may have a straight shape, but may also have a curved shape. The lattice is not necessarily made of longitudinal beams or the like, and may for example consist of interconnected spheres, pyramids, etc. among others.

Figure 2A:
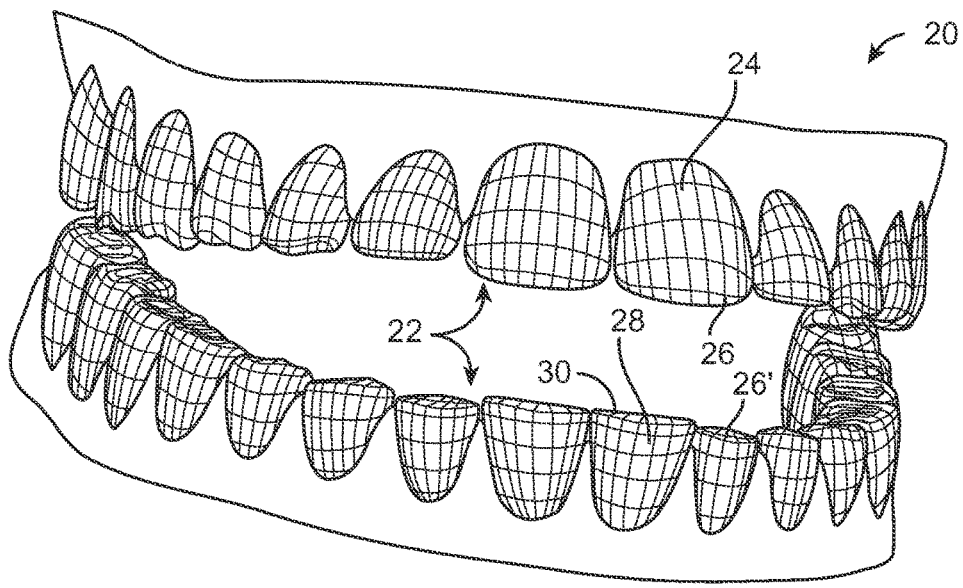
FIG. 2A shows a perspective view of an example of a basic structure formed into a bottom half and a top half for a dental appliance utilizing a lattice structure which may be used in a 3D printing process.
Figure 2B:
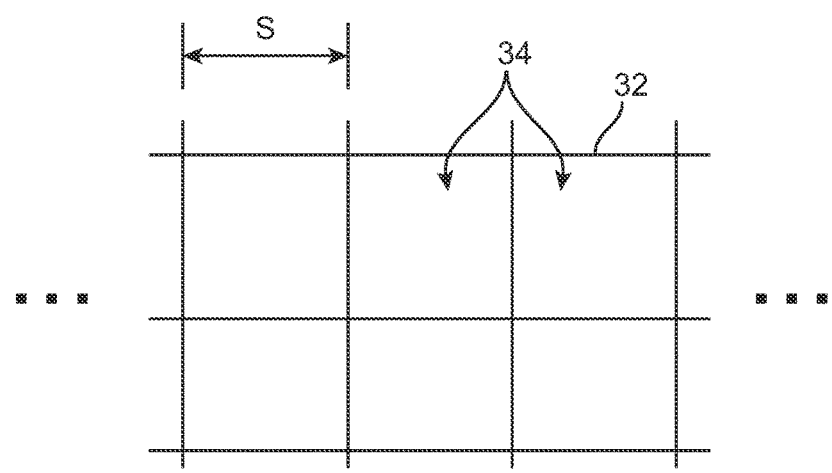
FIG. 2B shows a detail exemplary view of the openings in a lattice structure.

The lattice structure is typically a framework which contains a regular, repeating pattern as shown in FIG. 2A, wherein the pattern can be defined by a certain unit cell. A unit cell is the simplest repeat unit of the pattern. Thus, the lattice structure 24 is defined by a plurality of unit cells. The unit cell shape may depend on the required stiffness and can for example be triclinic, monoclinic, orthorhombic, tetragonal, rhombohedral, hexagonal or cubic. Typically, the unit cells of the lattice structures have a volume ranging from, e.g., 1 to 8000 mm$^3$, or preferably from 8 to 3375 mm$^3$, or more preferably from 64 to 3375 mm$^3$, or most preferably from 64 to 1728 mm$^3$. The unit cell size may determine, along with other factors such as material choice and unit cell geometry, the rigidity (stiffness) and transparency of the free-form structure. Larger unit cells generally decrease rigidity and increase transparency, while smaller unit cells typically increase rigidity and decrease transparency. Local variations in the unit cell geometry and/or unit cell size may occur, in order to provide regions with a certain stiffness. Therefore, the lattice 24 may comprise one or more repeated unit cells and one or more unique unit cells. In order to ensure the stability of the lattice structure 24, the strips, bars, girders, beams or the like may have a thickness or diameter of, e.g., 0.1 mm or more. In particular embodiments, the strips, bars, girders, beams or the like may preferably have a thickness or diameter of, e.g., 0.2 mm, 0.4 mm, 0.6 mm, 0.8 mm, 1 mm, 1.5 mm, 2 mm, 3 mm, 5 mm or more. The main function of the lattice structure 24 is to ensure a certain stiffness of the free-form structure. The lattice structure 24 may further enhance or ensure transparency, as it is an open framework. The lattice structure 24 can preferably be considered as a reticulated structure having the form and/or appearance of e.g., a net or grid, although other embodiments may be used.

The stiffness of the lattice structure depends on factors such as the structure density, which depends on the unit cell geometry, the unit cell dimensions and the dimensions of the strips, bars, girders, beams, etc. of the framework 32. Another factor is the distance, S, between the strips and the like, or in other words, the dimensions of the openings in the lattice structure, as shown in the detail exemplary view of FIG. 2B. Indeed, the lattice structure is an open framework and therefore comprises openings 34. In particular embodiments, the opening size S of the lattice structure is between, e,g., 1 and 20 mm, between 2 and 15 mm, or between 4 and 15 mm. In preferred embodiments, the opening size is between, e.g., 4 and 12 mm. The size of the openings may be the equal to or smaller than the size of the unit cell 34 while in other embodiments, the openings may be uniform in size or arbitrary in size. In yet another alternative, differing regions of the lattice may have openings which are uniform in size but which are different from other regions.

Figure 2C:
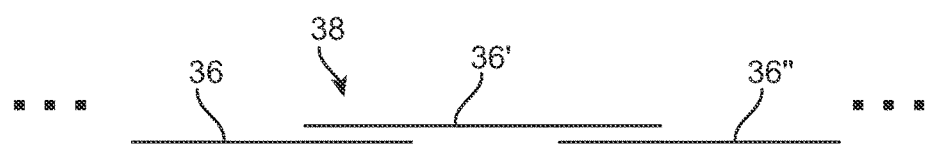
FIG. 2C shows an exemplary end view of a lattice structure having several reticulated layers.

In particular embodiments, the free-form structures may comprise to lattice structure having one or more interconnected reticulated layers, as shown in the exemplary end view of FIG. 2C. For instance, the lattice structure may comprise one, two, three or more reticulated layers 38, where the structure comprises different at least partially superimposed and/or interconnected layers 36, 36', 36" within the lattice structure. The degree of stiffness provided by the lattice structure may increase with the number of reticulated layers provided therein. In further particular embodiments, the free-form structures may comprise more than one lattice structure. The examples shown are merely illustrative of the different embodiments.

For certain applications the lattice structure may further comprise one or more holes with a larger size than the openings or unit cells as described hereinabove. Additionally or alternatively, the lattice structure may not extend over the entire shape of the free-form structure such that openings in the structure or regions for handling, tabs or ridges, and/or regions of unsupported coating material are formed. An example of such an application is a facial mask, where holes are provided at the location of the eyes, mouth and/or nose holes. Typically, these latter holes are also not filled by the coating material.

Similarly, in particular embodiments, the size of the openings which are impregnated in and/or enclosed by the adjoining material may range between, e.g., 1 and 20 mm. The holes in the lattice structure (corresponding to holes in the free-form structure) as described herein will also typically have a size which is larger than the unit cell. Accordingly, in particular embodiments, the unit cell size ranges between, e.g., 1 and 20 min.

According to particular embodiments, as shown in the end view of FIG. 2D, the envisaged free-form structure may contain regions 33 comprised only of the coating material 31. This may be of interest in areas where extreme flexibility of the free-form structure is desired.

In particular embodiments, the envisaged free-form structure may comprise a basic structure which contains, in addition to a lattice structure, one or more limited regions which do not contain a lattice structure, but are uniform surfaces, as shown in the detail perspective view of FIG. 2E. Typically these form extensions 35 from the lattice structure with a symmetrical shape (e.g. rectangular, semi-circle, etc.). Such regions, however, typically encompass less than, e.g., 50%, or more particularly less than, e.g., 30%, or most particularly less than, e.g., 20% of the complete basic structure. Typically they are used as areas for handling (manual tabs) of the structure and/or for placement of attachment structures (clips, elastic string, etc.). In particular embodiments, the basic structure may be comprised essentially of only a lattice structure.

It can be advantageous for the dental appliance structure to have certain regions with a different stiffness (such as in the molar teeth to provide added force). This can be achieved by providing a lattice structure with locally varying unit cell geometries, varying unit cell dimensions and/or varying densities and/or varying thicknesses of the lattice structure (by increasing the number of reticulated layers), as shown in the exemplary detail perspective view of FIG. 2F. Accordingly, in particular embodiments, the lattice structure is provided with varying unit cell geometries, varying unit cell dimensions, varying lattice structure thicknesses and/or varying densities 37, 39. Additionally or alternatively, as described herein, the thickness of the coating material may also be varied, as shown in FIG. 2G. Thus, in particular embodiments, the free-form structure has a varying thickness with a region of first thickness 41 and a region of second thickness 43. In further particular embodiments, the free-form structures may have regions with a different stiffness, while they retain the same volume and external dimensions.

In particular embodiments of the free-form structures, the basic structure or the lattice structure can be covered in part with a coating material which is different from the material used for manufacturing the lattice structure. In particular embodiments the lattice structure is at least partly embedded within or enclosed by (and optionally impregnated with) the coating material, as shown in the exemplary detail end view of FIG. 2H. In further embodiments, the coating material is provided onto one or both surfaces of the lattice structure 36. In particular embodiments only certain surface regions of the basic structure and/or the lattice structure in the free-form structure are provided with a coating material while portions may be exposed 45. In particular embodiments, at least one surface of the basic structure and/or lattice structure may be coated 31 for at least 50%, more particularly at least 80%. In further embodiments, all regions of the basic structure having a lattice structure are fully coated, on at least one side, with the coating material. In further particular embodiments, the basic structure is completely embedded with the coating material, with the exceptions of the tabs provided for handling.

In further embodiments, the free-form structure comprises, in addition to a coated lattice structure, regions of coating material not supported by a basic structure and/or a lattice structure.

Accordingly, in particular embodiments, the free-form structure may comprise at least two materials with different texture or composition. In other embodiments, the free-form structure may comprise a composite structure, e.g., a structure which is made up of at least two distinct compositions and/or materials.

The coating material(s) may be a polymeric material, a ceramic material and/or a metal. In particular embodiments, the coating material(s) is a polymeric material. Suitable polymers include, but are not limited to, silicones, a natural or synthetic rubber or latex, polyvinylchloride, polyethylene, polypropylene, polyurethanes, polystyrene, polyamides, polyesters, polyepoxides, aramides, polyethyleneterephthalate, polymethylmethacrylate, ethylene vinyl acetate or blends thereof. In particular embodiments, the polymeric material comprises silicone, polyurethane, polyepoxide, polyamides, or blends thereof.

In particular embodiments the free-form structures comprise more than one coating material or combinations of different coating materials.

In specific embodiments, the coating material is a silicone. Silicones are typically inert, which facilitates cleaning of the free-form structure.

In particular embodiments, the coating material is an optically transparent polymeric material. The term "optically transparent" as used herein means that a layer of this material with a thickness of 5 mm can be seen through based upon unaided, visual inspection. Preferably, such a layer has the property of transmitting at least 70% of the incident visible light (electromagnetic radiation with a wavelength between 400 and 760 nm) without diffusing it. The transmission of visible light, and therefore the transparency, can be measured using a UV-Vis Spectrophotometer as known to the person skilled in the art. Transparent materials are especially useful when the free-form structure is used for wound treatment (see further). The polymers may be derived from one type of monomer, oligomer or prepolymer and optionally other additives, or may be derived from a mixture of monomers, oligomers, prepolymers and optionally other additives. The optional additives may comprise a blowing agent and/or one or more compounds capable of generating a blowing agent. Blowing agents are typically used for the production of a foam.

Accordingly, in particular embodiments, the coating material(s) are present in the free-form structure in the form of a foam, preferably a foamed solid. Thus, in particular embodiments, the lattice structure is coated with a foamed solid. Foamed materials have certain advantages over solid materials: foamed materials have a lower density, require less material, and have better insulating properties than solid materials. Foamed solids are also excellent impact energy absorbing materials and are therefore especially useful for the manufacture of free-form structures which are protective elements (see further). The foamed solid may comprise a polymeric material, a ceramic material or a metal. Preferably, the foamed solid comprises one or more polymeric materials.

The foams may be open cell structured foams (also known as reticulated foams) or closed cell foams. Open cell structured foams contain pores that are connected to each other and form an interconnected network which is relatively soft. Closed cell foams do not have interconnected pores and are generally denser and stronger than open cell structured foams. In particular embodiments, the foam is an "integral skin foam", also known as "self-skin foam", e.g., a type of foam with a high-density skin and a low-density core.

Thus in particular embodiments, free-form structures may comprise a basic structure which includes a lattice structure which is at least partially coated by a polymeric or other material as described herein. For some applications, the thickness of the coating layer and the uniformity of the layer thickness of the coating are not essential. However, for certain applications, it can be useful to provide a layer of coating material with an adjusted layer thickness in one or more locations of the free-form structure, for example, to increase the flexibility of the fit of the free-form structure on the body part.

Figure 2I:
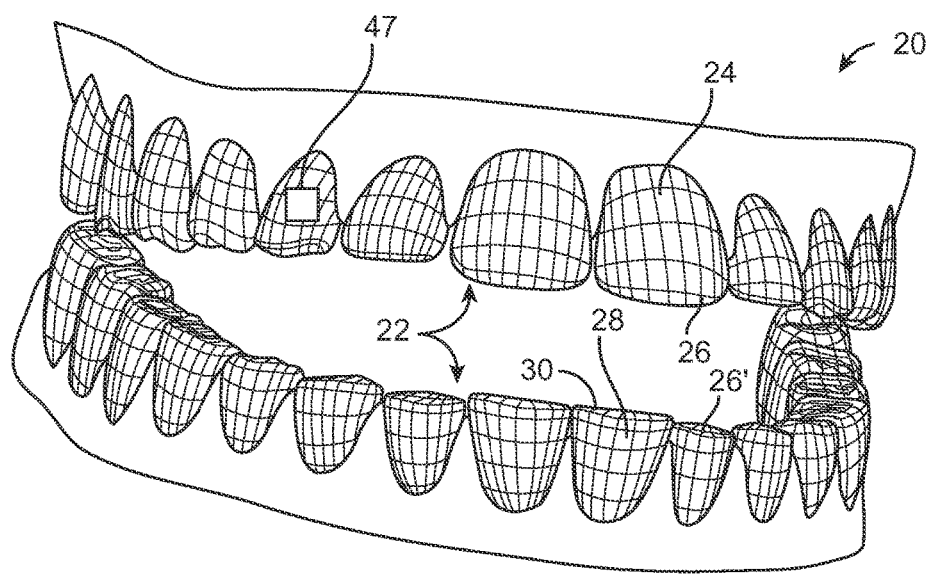
FIG. 2I shows a perspective view of an aligner having at least one additional component integrated.
Figure 2J:
FIG. 2J shows an exemplary end view of a lattice structure a hinge or other movable mechanism integrated along the lattice.

The basic structure of the freeform structures envisaged herein can be made as a single rigid free-form part which does not need a separate liner or other elements. Independent thereof it is envisaged that the free-form structures can be further provided with additional components 47 such as sensors, straps, or other features for maintaining the structure in position on the body, or any other feature that may be of interest in the context of the use of the structures and integrated within or along the structure, as shown in FIG. 2I. Various examples of sensors which may be integrated are described in further detail herein.

In certain embodiments, the free-form structure comprises a single rigid lattice structure (optionally comprising different interconnected layers of reticulated material). However, such structures often only allow a limited flexibility, which may cause discomfort to a person or animal wearing the free-form structure. An increase in flexibility can be obtained if the free-form structure comprises two or more separate rigid lattice structures which can move relative to each other. These two or more lattice structures are then enclosed by a material as described above, such that the resulting free-form structure still is made or provided as a single part. The rigidity of the shape of the free-form structure is ensured locally by each of the lattice structures, while additional flexibility during placement is ensured by the fact that there is a (limited) movement of the lattice structures relative to each other. Indeed, in these embodiments, the coating material and/or a more limited lattice structure) will typically ensure that the lattice structures remain attached to each other.

In particular embodiments, the lattice structures are partially or completely overlapping. However, in particular embodiments, the different lattice structures are non-overlapping. In further particular embodiments, the lattice structures are movably connected to each other, for example via a hinge or other movable mechanism 49, 49', as shown in the detail end view of FIG. 2J. In particular embodiments the connection is ensured by lattice material. In further particular embodiments the lattice structures may be interconnected by one or more beams which form extensions of the lattice structures. In further embodiments the lattice structures are held together in the free-form structure by the coating material. An example of such a free-form structure is a facial mask with a jaw structure that is movable with respect to the rest of the mask. Accordingly, in particular embodiments, the lattice structure comprises at least two separate lattice structures movably connected to each other, whereby the lattice structures are integrated into the free-form structure, as shown.

The free-form structure may be used for wound treatment as described herein. For optimal healing, the free-form structure provides a uniform contact and/or pressure on the wound site or specific locations of the wound site. The lattice structure makes it simple to incorporate pressure sensors into the free-form structure according to the present invention. The sensors can be external sensors, but may also be internal sensors. Indeed, the lattice structure can be designed such that it allows mounting various sensors at precise locations, as described above, before impregnating and/or enclosing the lattice structure by a polymer or other material.

Additionally or alternatively, the free-form structure may comprise one or more other sensors, as described above in FIG. 2I, such as a temperature sensor, a moisture sensor, an optical sensor, a strain gauge, an accelerometer, a gyroscope, a GPS sensor, a step counter, etc. Accelerometers, gyroscopes, GPS sensors and/or step counter may for example be used as an activity monitor. Temperature sensor(s), moisture sensor(s), strain gauge(s) and/or optical sensor(s) may be used to monitor the healing process during wound treatment. Specifically, the optical sensor(s) may be used to determine collagen fiber structure as explained in US Pat. App. 2011/0015591, which is hereby incorporated by reference in its entirety and for any purpose.

Accordingly, in particular embodiments the free-form structure further comprises one or more external and/or internal sensors. In specific embodiments, the free-form structure comprises one or more internal sensors. In certain embodiments, the free-form structure comprises one or more pressure and/or temperature sensors.

The skilled person will understand that in addition to the sensor(s), also associated power sources and/or means for transmitting signals from the sensor(s) to a receiving device may be incorporated into the free-form structure, such as wiring, radio transmitters, infrared transmitters, and the like.

In particular embodiments, at least one sensor may comprise micro-electronic mechanical systems (MEMS) technology, e.g., technology which integrates mechanical systems and micro-electronics. Sensors based on MEMS technology are also referred to as MEMS-sensors and such sensors are small and light, and consume relatively little power. Non-limiting examples of suitable MEMS-sensors are the STTS751 temperature sensor and the LIS302DL accelerometer STMicroelectronics.

Figure 2K:
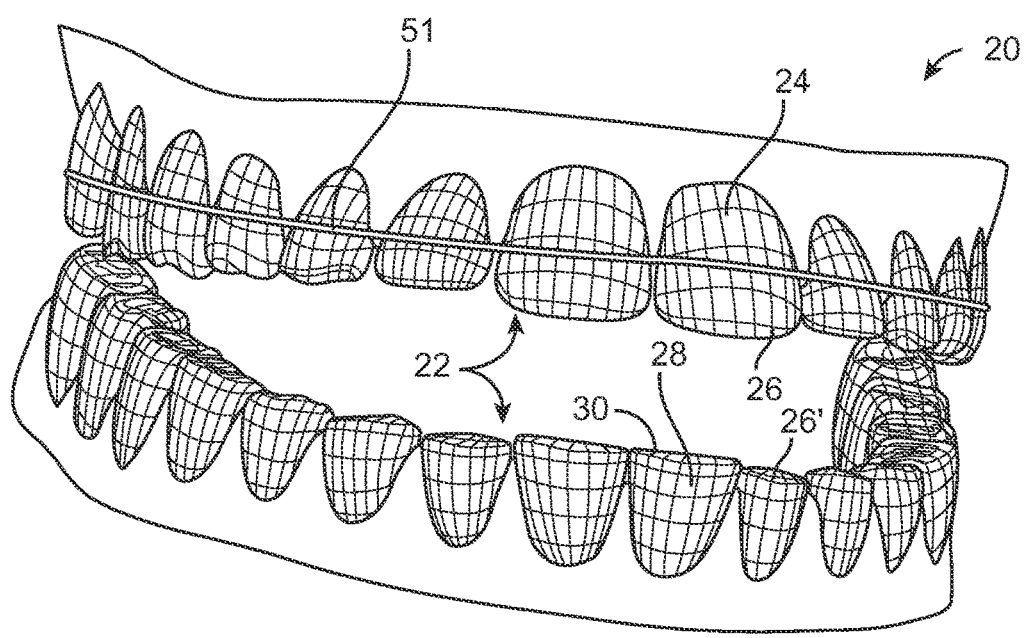
FIG. 2K shows a perspective view of an aligner having one or more (internal) channels integrated.

As shown in FIG. 2K, the lattice structure also allows providing the free-form structure with one or more (internal) channels 51. These channels may be used for the delivery of treatment agents to the underlying skin, tissue, or teeth. The channels may also be used for the circulation of fluids, such as heating or cooling fluids.

One philosophy of orthodontic treatment is known as "Differential Force" called out for the corrective forces directed to teeth to be closely tailored according to the ideal force level requirements of each tooth. The Differential Force approach was supported by hardware based on calibrated springs intended to provide only those ideal force levels required. Carrying the concepts of the Differential Force approach forward to the precepts of aligner fabrication, one can appreciate that CNC-machined aligners exhibiting carefully controlled variable thickness can accomplish the Differential Force objectives on a tooth-by-tooth basis. The compartments surrounding teeth can have wall thicknesses established at the CAD/CAM level by a technician based on the needs of each tooth. A 3D printed aligner can have a limitless series of regions, each with a unique offset thickness between its inner and outer surfaces.

Figure 3:
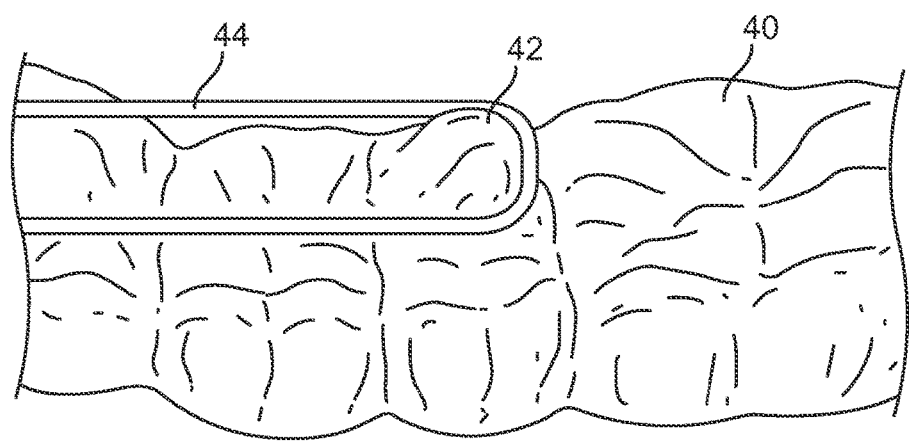
FIG. 3 shows a perspective detail view of a portion of an aligner having an area that is machined to have a relatively thicker material portion to accept an elastic.

Prior to installing such devices, a practitioner may assess the progress of a case at mid-treatment for example and in particular, make note of problem areas where the desired tooth response is lagging or instances where particular teeth are stubbornly not moving in response to treatment forces. The 3D printed structure can include a group of small devices that are intended to be strategically positioned and 3D printed with an aligner's structure. Such devices are termed "aligner auxiliaries." FIG. 3 is a detail view of a portion of an aligner 40 showing a 3D printed area 42 that is machined allowing thicker material to accept an elastic 44. Other 3D printed geometries of interest would be divots or pressure points, creating openings/windows on the aligner for a combination treatment, e.g., forming hooks on the aligner for elastic bands, among others. Aligner auxiliaries may be installed in those locations to amplify and focus corrective forces of the aligner to enhance correction. For example, an auxiliary known as a tack can be installed after a hole of a predetermined diameter is pierced through a wall of a tooth-containing compartment of an aligner. The diameter of the hole may be slightly less than the diameter of a shank portion of the tack which may be printed directly on the aligner. Such progressively-sized tacks and other auxiliary devices are commercially available to orthodontists who use them to augment and extend the tooth position correcting forces of aligners.

Figures 4A, 4B:
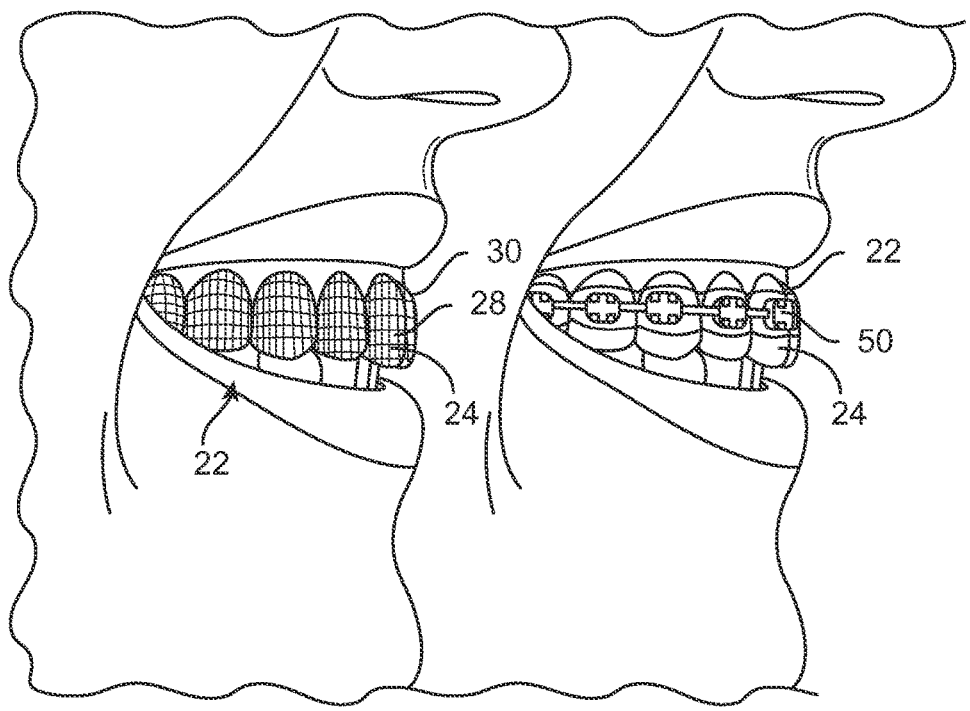
FIGS. 4A and 4B illustrate a variation of a free-form dental appliance structure having a relatively rigid lattice structure and one or more features for use as a dental appliance or retainer.

Bumps can also be used and serve to focus energy stored locally in the region of the aligner's structure adjacent to a bump. The inward-projecting bump causes an outward flexing of the aligner material in a region away from the tooth surface. Configured in this way, bumps gather stored energy from a wider area and impinge that energy onto the tooth at the most mechanically advantageous point, thus focusing corrective forces most efficiently. An elastic hook feature 50 can be 3D printed directly in an otherwise featureless area of an aligner's structure, as shown in the side views of FIGS. 4A and 4B. Elastic hooks may also be used as anchor points for orthodontic elastics that provide tractive forces between sectioned portions of an aligner (or an aligner and other structures fixedly attached to the teeth) as needed during treatment.

Figure 4C:
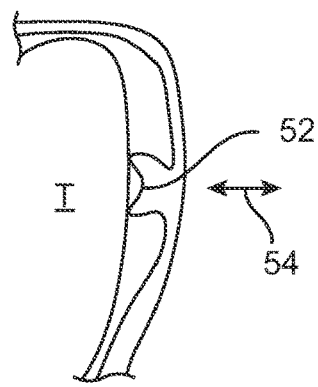
FIG. 4C shows a partial cross-sectional view of as suction feature fabricated to adhere to one or more particular teeth.

Aside from hook features 50, other features such as suction features 52 may be fabricated for adherence to one or more particular teeth T, as shown in the partial cross-sectional view of FIG. 4C. In this manner, the aligner may exert a directed force 54 concentrated on the one or more particular teeth.

Figure 4D:
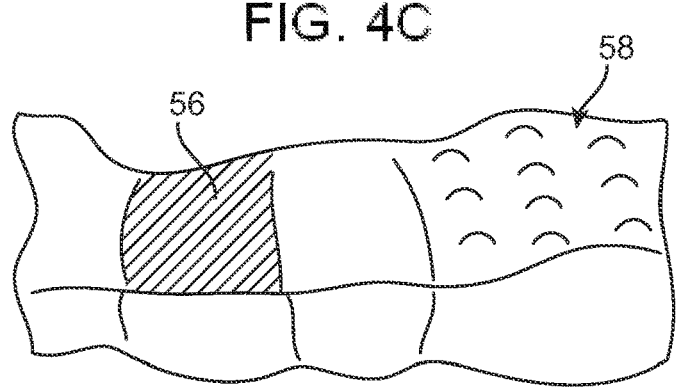
FIG. 4D shows a perspective view of a portion of the aligner having regions configured to facilitate eating or talking by the patient.

In yet another embodiment, as shown in the perspective view of FIG. 4D, the occlusal surfaces of the aligner may be fabricated to have areas defined to facilitate eating or talking by the patient. Such features may include occlusal regions which are thinned, made into flattened surfaces 56, or made with any number of projections 58 to facilitate eating.

Figure 4E:
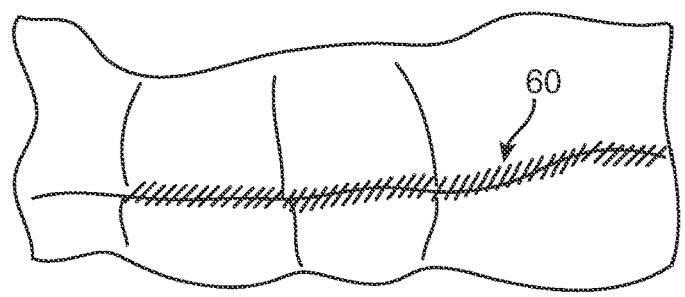
FIG. 4E shows a perspective view of a portion of the aligner having different portions fabricated to have different areas of varying friction.

Additionally, different portions of the aligners may be fabricated to have different areas 60 of varying friction, as shown in the perspective view of FIG. 4E. Such varying areas may be formed, e.g., along the edges to prevent tearing of the aligner material.

Figure 4F:
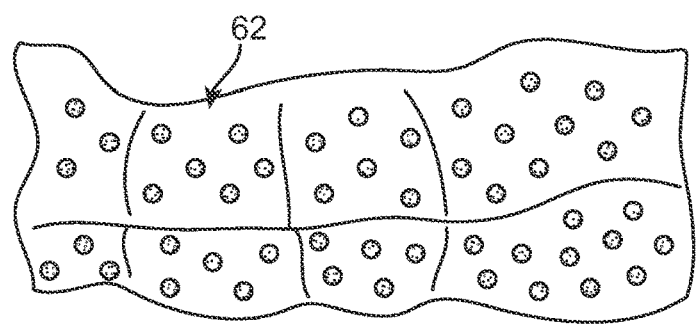
FIG. 4F shows a perspective view of a portion of the aligner having a particulate coating.

Additional attachments can be formed on the 3D printed dental appliances such as particulate coatings. The particulate coating 62 may be formed on the tooth engaging surface of the lattice 3D printed appliance in any convenient manner, e.g., fusion, sintering, etc., as shown in the perspective view of FIG. 4F. The particles making up the coating may be any convenient shape, including a spherical shape or an irregular shape, and may be constructed of metal (including alloys), ceramic, polymer, or a mixture of materials. The particulate coating adhered to the tooth engaging surface may take the form of discrete particles which are spaced apart from each other on the surface, or the form of a layer or multiple layers of particles bonded together to produce a network of interconnected pores. The particulate coating provides a porous interface into which a fluid bonding resin may readily flow and penetrate. Upon curing of the resin to solid form, mechanical interlock is achieved between the cured resin and the particulate coating. Under some circumstances chemical bonding in addition to this mechanical bonding may be achieved, e.g., by the use of polycarboxylate or glass ionomer cements with stainless steel and other metallic substrates and with ceramic substrates.

For a coating of integrally-joined particles which make up a porous structure having a plurality of interconnected pores extending therethrough, the particles are usually about −100 mesh and preferably a mixture of particles of varying particle sizes restricted to one of three size ranges, e.g., −100+325 mesh (about 50 to about 200 microns), −325+500 mesh (about 20 to about 50 microns), and −500 mesh (less than about 20 microns). The size of the particles in the porous structure determines the pore size of the pores between the particles. Smaller-sized pores are preferred for fluid resin bonding agents whereas larger-sized pores are preferred for more viscous cementitious bonding materials. The selection of particle size is also used to control the porosity of the coating to within the range of about 10 to about 50% by volume.

An adequate structural strength is required for the composite of substrate and coating, so that any fracture of the joint of the bracket to the tooth occurs in the resin and not in the coating. To achieve this condition, the structural strength of the coating, the interface between the coating and the substrate and the substrate itself is at least 8 MPa.

FIGS. 5A to 5D show exploded views of alternative lattice structures which may be utilized in any of the embodiments described herein. The lattice structures have open faces and are layered and can also be regarded as two or more interconnected reticulated layers or as structures comprising only one layer or more than two layers.

Figure 5A:
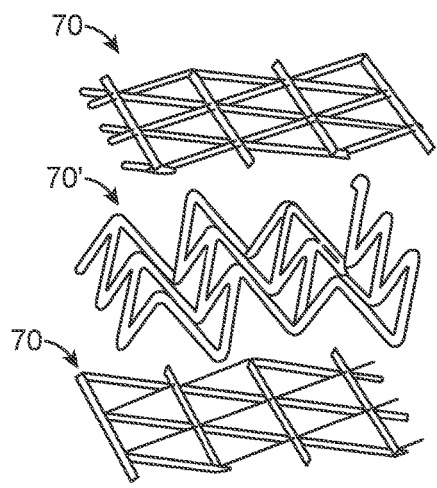
FIGS. 5A to 5D show various views of examples of lattice structures suitable for forming dental appliances.
Figure 5B:
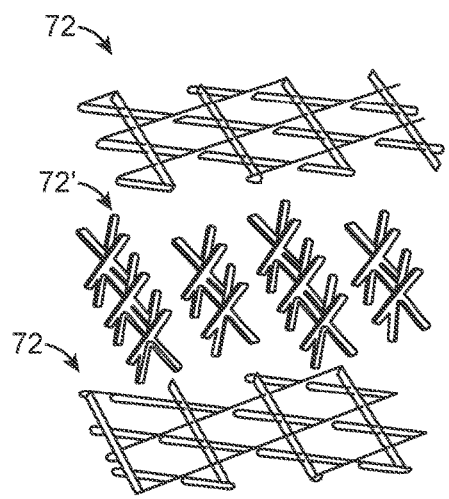
Figure 5C:
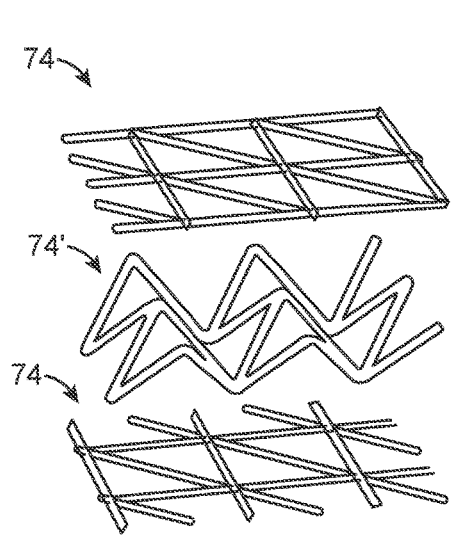
Figure 5D:
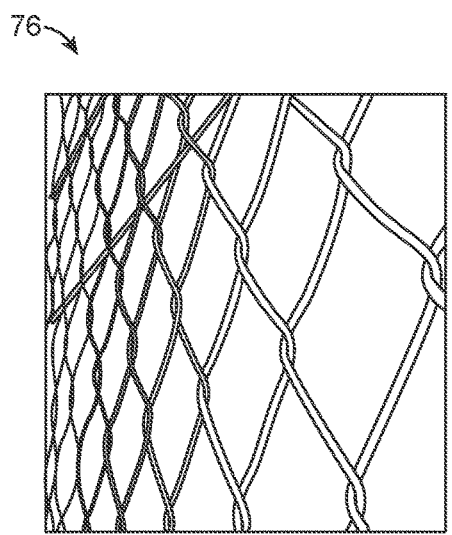

FIG. 5A shows a first and second perspective view of the lattice structure 70 having a triangular cell pattern and an example of the structure 70 reconfigured into an alternative or compressed configuration 70'. FIG. 5B shows a first and second perspective view of the lattice structure 72 having a polygonal cell pattern and an example of the structure 72 reconfigured into an alternative or compressed configuration 72'. FIG. 5C shows a first and second perspective view of the lattice structure 74 having a diamond cell pattern and an example of the structure 74 reconfigured into an alternative or compressed configuration 74'. FIG. 5D shows a perspective view of the lattice structure 76 having a linked diamond cell pattern.

The applications of the devices and methods discussed above are not limited to the use on the dentition but may include any number of further treatment applications. Moreover, such devices and methods may be applied to other treatment sites within the body. Modification of the above-described assemblies and methods for carrying out the invention, combinations between different variations as practicable, and variations of aspects of the invention that are obvious to those of skill in the art are intended to be within the scope of the claims.

What is claimed is:

1. A method for fabricating an oral appliance, comprising:
    capturing a three-dimensional representation of a dentition of a subject;
    generating a free-form structure having a polymeric lattice structure via three-dimensional printing, wherein the lattice structure is based on the three-dimensional representation and is complementary to at least part of a surface of the dentition, wherein the lattice structure defines a plurality of open spaces such that the free-form structure is at least partially transparent; and
    manufacturing the lattice structure by impregnating or covering a coating into or upon the lattice structure such that the oral appliance is formed.

2. The method of claim 1 further comprising generating one or more additional free-form structures and further manufacturing the one or more additional free-form structures to form one or more additional oral appliances, wherein each of the one or more additional oral appliances are configured to correct for malocclusions within the dentition.

3. The method of claim 1 wherein generating a free-form structure further comprises determining a force required to move a tooth and modifying a thickness of the free-form structure in proximity to the tooth.

4. The method of claim 3 wherein determining a force comprises performing a simulation to confirm a stress point for the free-form structure in proximity to the tooth.

5. The method of claim 1 wherein generating a free-form structure comprises having the lattice structure define a plurality of open spaces which are uniform to one another.

6. The method of claim 1 wherein generating a free-form structure comprises having the lattice structure define a plurality of open spaces which vary relative to one another.

7. The method of claim 1 wherein generating a free-form structure comprises having two or more lattice structures in proximity to one another.

8. The method of claim 1 wherein generating a free-form structure comprises varying a thickness of the lattice structure.

9. The method of claim 1 wherein manufacturing the lattice structure comprises varying a thickness of the coating.

10. The method of claim 1 wherein manufacturing the lattice structure further comprises defining one or more features upon the oral appliance.

11. The method of claim 10 wherein the one or more features comprises regions of varied friction over a surface of the oral appliance.

12. The method of claim 10 wherein the one or more features comprises projections extending from a surface of the oral appliance.

13. The method of claim 1 wherein manufacturing the lattice structure comprises impregnating or covering a portion of the lattice structure with a polymeric material.

14. The method of claim 1 wherein manufacturing the lattice structure comprises impregnating or covering the lattice structure with a particulate coating.

15. The method of claim 1 further comprising forming one or more channels through the coating.

16. The method of claim 1 further comprising integrating one or more sensors within or upon the oral appliance.

17. The method of claim 16 further comprising sensing forces on the lattice structure via the one or more sensors.

* * * * *